United States Patent
Bernard et al.

(10) Patent No.: US 10,119,922 B2
(45) Date of Patent: Nov. 6, 2018

(54) TEST PATTERN AND METHOD FOR CALIBRATING AN X-RAY IMAGING DEVICE

(71) Applicant: THALES, Courbevoie (FR)

(72) Inventors: Guillaume Bernard, Voreppe (FR); Albert Murienne, Grenoble (FR)

(73) Assignee: THALES, Courbevoie (FR)

( * ) Notice: Subject to any disclaimer, the term of this patent is extended or adjusted under 35 U.S.C. 154(b) by 171 days.

(21) Appl. No.: 15/251,967

(22) Filed: Aug. 30, 2016

(65) Prior Publication Data

US 2017/0074808 A1    Mar. 16, 2017

(30) Foreign Application Priority Data

Sep. 11, 2015    (FR) ..................................... 15 01892

(51) Int. Cl.
| | | |
|---|---|---|
| G01N 23/04 | (2018.01) | |
| A61B 6/03 | (2006.01) | |
| A61B 6/00 | (2006.01) | |

(52) U.S. Cl.
CPC ............. *G01N 23/04* (2013.01); *A61B 6/032* (2013.01); *A61B 6/583* (2013.01); *A61B 6/584* (2013.01); *G01N 2223/303* (2013.01)

(58) Field of Classification Search
CPC ......... A61B 6/032; A61B 6/583; A61B 6/584; G01N 2223/303; G01N 23/04
See application file for complete search history.

(56) References Cited

U.S. PATENT DOCUMENTS

| | | | |
|---|---|---|---|
| 5,442,674 A * | 8/1995 | Picard | A61B 6/583 378/18 |
| 6,044,132 A | 3/2000 | Navab | |
| 6,715,918 B2 | 4/2004 | Mitschke et al. | |
| 2005/0094771 A1 | 5/2005 | Basu et al. | |
| 2005/0147206 A1 | 7/2005 | Skalli et al. | |
| 2007/0122020 A1* | 5/2007 | Claus | A61B 6/583 382/131 |
| 2009/0067583 A1* | 3/2009 | Vogt | G01N 23/046 378/207 |
| 2010/0046718 A1 | 2/2010 | Weiser et al. | |

(Continued)

*Primary Examiner* — Glen Kao
*Assistant Examiner* — Chih-Cheng Kao
(74) *Attorney, Agent, or Firm* — Baker & Hostetler LLP

(57) ABSTRACT

A test pattern geometrically calibrates an x-ray imaging device to generate three-dimensional images of an object by reconstruction based on two-dimensional projections of the object, the calibrating test pattern comprising a volume support with markers having a radiological absorbance providing contrast to the volume support, the markers distributed in a three-dimensional pattern, in subsets substantially in parallel respective straight lines wherein sequences of cross-ratios are constructed from the respective subsets of markers. Each sequence of cross-ratios comprises a single cross-ratio for each quadruplet of markers in which quadruplet the markers are ordered depending on rank number of respective markers along the straight line they are aligned in a predefined first direction, the order being common to all cross-ratios. When a subset of markers comprises at least five markers, the order of the cross-ratios in the respective sequences of cross-ratios is defined by a rule common to all sequences of cross-ratios.

12 Claims, 3 Drawing Sheets

(56) References Cited

U.S. PATENT DOCUMENTS

2014/0114173 A1   4/2014  Bar-Tal et al.
2015/0272535 A1*  10/2015 Joson .................... A61B 6/025
                                                    382/131
2017/0020481 A1*  1/2017  Hawker ................ A61B 6/583

* cited by examiner

TEST PATTERN AND METHOD FOR CALIBRATING AN X-RAY IMAGING DEVICE

CROSS-REFERENCE TO RELATED APPLICATION

This application claims priority to foreign French patent application No. FR 1501892, filed on Sep. 11, 2015, the disclosure of which is incorporated by reference in its entirety.

FIELD OF THE INVENTION

The present invention relates to a device for geometric calibration of an x-ray imaging device. It more particularly relates to imaging devices the detector of which is two-dimensional, i.e. substantially planar. Imaging devices conventionally comprise an x-ray source and a two-dimensional detector. The x-rays are attenuated by a body to be imaged. The remaining energy is sensed by the detector and is converted into signals so as to produce a radiological image. The radiological image is a two-dimensional (2D) image (or projection) of an object deployed in a three-dimensional (3D) space interposed between the x-ray source and the two-dimensional detector. Conventionally, the x-ray source and the detector are installed on a device allowing them to be moved with respect to the body to be imaged so as to produce a plurality of projections of the body at different viewing angles. The projections are then used to reconstruct a three-dimensional image of the imaged body. During the image capturing process, the detector and the source must normally follow predetermined paths, circular paths for example. However, because of tolerances of the moving device, there are errors between the path actually followed by each of these elements and the ideal path that it should follow. In other words, there are errors between the ideal positions of the source and/or detector with respect to the object and the positions that they actually occupy. The reconstruction of the 3D image from the 2D projections of the object takes into account the relative positions of the object, the detector and the source on each image capture. It is therefore essential to take into account the positioning errors defined above if 3D images having a good resolution and a good precision are to be obtained. In other words, it is essential to know the geometric characteristics that the x-ray imaging device had during the acquisition of each 2D projection from which the 3D image is constructed. The calibrating device allowing these positioning errors to be taken into account is conventionally based on the use, in the 3D space, of a known calibrating geometric test pattern. The calibrating test pattern comprises a known object comprising a certain number of markers (radio-opaque markers) the positions of which in the space are known by construction by coordinates measured with respect to a coordinate system specific to this object. A projection of the test pattern is acquired under the geometric conditions that it is desired to calibrate, i.e. from the viewpoint that it is desired to calibrate. This viewpoint is defined by the positions of the detector, of the source and of the test pattern and by their relative orientations. The projections of the markers are recognized in the projection of the test pattern. The positions of the projections of the markers in the projection of the test pattern and knowledge of their respective positions in the test pattern allow, depending on the adopted view point, the geometric characteristics that the imaging device had during the acquisition of the image to be determined. The geometric characteristics that the x-ray imaging device had during the acquisition of an image from an adopted view point are defined by a 4×3 projection matrix that allows each point of the object in the 3D space (with respect to the terrestrial reference frame) to be matched with its projection on a planar 2D detector (with respect to a frame of reference associated with the detector). These geometric characteristics are advantageously used in the 3D reconstructing step.

BACKGROUND

Conventional test patterns comprise a cylindrical object that is transparent to x-rays, which object is equipped on its surface with radio-opaque balls forming the markers. The balls are conventionally spaced out along a spiral. However, this type of arrangement does not allow many balls to be integrated into the cylindrical object, this adversely affecting the precision of the calibration and therefore the reconstruction of the 3D image.

The test pattern is conventionally equipped with a reference ball having a different size from the other balls. The positions of the other balls relative to this reference ball are known. It is the identification and the position of the projection of this reference ball in a 2D image, knowledge of the positions of the other balls with respect to the reference ball and the positions of the projections of the other balls with respect to the projection of the reference ball that allow the positions of the projections of all the balls in the image and their positions in the 3D space to be matched and thus the projection matrix to be obtained by means of suitable algorithms. The presence and identification of the projection of the reference ball in the projection of the object is therefore of fundamental importance. However, if the projection of this ball is superposed on that of another ball in an image, this possibly being the case for certain viewing angles, if the projection of this ball does not appear in the image, this possibly being the case if the image of the test pattern is truncated, or indeed if the image is of poor quality, it is then possible to attribute, to a projection detected in a 2D image, the wrong ball of the 3D space, or to find it impossible to attribute the corresponding balls to the projections. The calibration is then impossible or erroneous. In other words, this type of test pattern leads to calibrating methods that lack robustness with respect to erroneous identification of the projection of the reference ball (false detections). Moreover, it may prove to be complex and expensive to identify, with a good confidence level, the projection of the reference ball from a set of projections of balls.

A test pattern that does not require a reference ball to be identified is known from United States patent U.S. Pat. Ser. No. 6,715,918. This test pattern comprises a cylindrical body and markers arranged along a spiral. The markers comprise two types of markers that are differentiated by their geometric properties, for example their respective sizes and/or shapes. A binary value is associated with each of the two types of physical markers. The values assigned to a sequence of successive markers then form a binary code. Markers of the first and second type are arranged in a spiral so that when a preset number of successive markers is considered, the binary code obtained appears only once along the spiral whatever the read-out direction. However, this test pattern has a certain number of drawbacks. Specifically, since the markers are differentiated by their geometric properties, and especially by their sizes, the closer a marker is to the x-ray source, the larger its projection. Therefore, it is not possible to guarantee, even if markers of very different sizes are provided, that the projections of the markers of the two types will be easily differentiable at each and every angle of image capture. There is therefore a nonzero risk that they will be mixed up in the projections obtained and an image of a marker of one type attributed to a marker of another type. This limits the reliability of the calibration.

The reliability of the calibration is also limited because of the spiral arrangement of the markers. When a light source illuminates the test pattern along a central axis perpendicular to the axis of the cylinder, the distances between the projections of the markers illuminated by the edges of the beam emitted by the source are very small and the images of these markers may be superposed. This makes the attribution of a projection of a marker to a given marker of the test pattern more difficult and less reliable, because of the complexity of the spiral shape, and limits the precision of the calibration. One solution given in patent U.S. Pat. Ser. No. 6,715,918 is to exclude the edges of the cylinder from the projection zone so as to prevent superposition of the projections of the markers. However, this solution, because it excludes certain markers from the projections, leads to a limited precision. Another solution given in patent U.S. Pat. Ser. No. 6,715, 918 is to make provision for a marker-detecting algorithm allowing the projections of markers located on the edges of the cylinder with respect to the central axis to be excluded from the calibration. However, this increases the complexity of the calibration and is not 100% reliable.

SUMMARY OF THE INVENTION

One aim of the invention is to remedy at least one of the aforementioned drawbacks.

To this end, one subject of the invention is a calibrating test pattern intended to geometrically calibrate an x-ray imaging device intended to generate three-dimensional images of an object by reconstruction based on two-dimensional projections of said object, the calibrating test pattern comprising a volume support equipped with markers having a radiological absorbance providing contrast with respect to the volume support, the markers being distributed in a three-dimensional pattern. The markers are distributed in subsets of markers distributed in substantially parallel respective straight lines so that sequences of cross-ratios may be constructed from the respective subsets of markers, each sequence of cross-ratios comprising a single cross-ratio for each quadruplet of markers, in which quadruplet the markers are ordered in an order depending on the rank number of the respective markers along the straight line on which they are aligned in a predefined first direction, said order being common to all the cross-ratios, and when a subset of markers comprises at least five markers, the order of the cross-ratios in the respective sequences of cross-ratios is defined by a predefined rule common to all the sequences of cross-ratios. Advantageously, the sequences of cross-ratios are all different.

The calibrating test pattern according to the invention allows robust, simple and reliable calibrating methods to be implemented. Specifically, a projection of a marker and the associated marker in the test pattern are matched from the positions of marker projections detected in an image (projection of the test pattern). However, the detection of projections of markers of the test pattern according to the invention is reliable. Specifically, it is independent of the size and shape of the markers. This detection may moreover be obtained using very simple detecting algorithms (of the circular-blob detector type). It is not necessary for these algorithms to be able to differentiate projections of markers of different geometries.

Moreover, markers and their respective projections in a 2D image or projection of the test pattern are not matched directly. They are matched by matching unique cross-ratio chains formed on the one hand by the projections of the markers and on the other hand by the markers of the test pattern. The risk of making an error during the matching process is therefore much lower than during a matching process carried out projection by projection. The test pattern according to the invention therefore makes it possible to implement robust detecting methods.

During an x-ray image capture, the geometric operation implemented is a conical projection (central projection) of the imaged body. The image of a straight line is a straight line and the cross-ratios between the distances are preserved by central projection. The risk of superposition of the images of the various markers on the border of a beam the central radius of which is substantially perpendicular to an axis perpendicular to the alignments of markers is therefore limited, thereby allowing a reliable calibration to be obtained. This property makes it possible to take into account the projections of all of the markers when performing the calibration, thereby allowing a precise calibration to be obtained. The distribution of the markers in parallel straight lines also promotes the precision and reliability of the calibration because the number of markers able to be integrated into a cylinder is high.

The distribution of the markers and therefore of the projections of the markers in straight lines allows the coded information formed by the projections of the markers, here the series of cross-ratios, to be easily extracted with a good reliability using a simple algorithm for detecting alignments in the 2D projections. It makes it possible to facilitate the matching, with a good degree of certainty, of sections of projected straight lines with the corresponding straight lines in the test pattern. Moreover, the known arrangement of the markers in straight lines and therefore the a priori arrangement of the projections of markers in straight lines may allow small errors in the positions of the projections of certain markers that are not on the expected straight line to be corrected and thus a precise calibration to be obtained.

The calibrating test pattern advantageously comprises one of the following features or a plurality of the following features:
  all the markers have substantially the same size and substantially the same shape;
  the straight lines are what are called observable generatrices of a cylinder;
  the distribution of the straight lines on which the subsets of markers are aligned is chosen so that, for all the projection conditions under which images are acquired during the calibration no marker projection overlaps another marker projection and/or so that if the marker projections issued from two subsets of markers do overlap, the projections of the markers of the other subsets of markers do not overlap;
  the subsets of markers are distributed in respective observable straight-line segments parallel to an axis, the straight-line segments being of same length and having the same coordinates along said axis, each straight-line segment accommodating a first integer m of sites capable of being occupied by a marker, any two consecutive sites considered along said observable segment being spaced apart by a predetermined distance called the pitch, each site respectively being assigned a first value or a second value depending on whether it is occupied by a marker or not, the markers being distributed so that the values attributed to a second integer n, at most equal to m, of any consecutive sites considered in a given direction along respective straight-line segments form respective binary codes composed of n bits, each binary code composed of n bits formed in said direction being unique;

the second number m is higher than the first number n;

the markers are distributed over the test pattern so that, for a known number of generatrices and of sites per generatrice, and for known degrees of occupation of the sites of respective generatrix, a difference between the binary codes formed by the values taken by the m consecutive sites accommodated by respective observable generatrices in the predefined direction is maximal, the binary codes being sections of a series obtained by means of a LFSR of n bits, m being lower than or equal to n;

the order of the cross-ratios in each cross-ratio sequence constructed from a subset of markers aligned on a straight line is defined in the following way:

--- for markers denoted $A_g$ having rank numbers $g = 1$ to N, where N is an integer,
along the straight line in a second direction,
  if i is from 1 to N−3 then:
    (-if j is from i+1 to N−2 then:
      (-if k is from j+1 to N−1 then:
        (-if l is from k+1 to N then:
          (-insert the following cross-ratio in the sequence, the following cross-ratio being a cross-ratio calculated with the markers $A_{g=i}$, $A_{g=j}$, $A_{g=k}$, $A_{g=l}$,
          − l=l+1)
        − k=k+1)
    − j=j+1),
  −i=i+1);

--- the order of the markers in each quadruplet of markers is the order of the markers along the straight line on which they are aligned in the first direction.

The invention also relates to a method for determining geometric characteristics of an x-ray imaging device intended to produce three-dimensional images of an object by reconstruction based on two-dimensional images of said object, said method using a calibrating test pattern according to the invention, the method according to the invention comprising the following steps:

placing the calibrating test pattern in a projection zone between an x-ray source and an x-ray detector;

acquiring at least one projection of the calibrating test pattern in at least one imaging-device geometry, which geometry is defined by the positions of the source, of the test pattern and of the detector and their relative orientations;

and, for each projection of the test pattern:
  detecting the projections of markers in the projection;
  determining the positions of the projections of markers in the projection;
  detecting alignments of projections of the markers in respective straight lines that are what are called image straight lines; and
  for each alignment of projections of markers:
    forming a sequence, which is what is called the image sequence, of cross-ratios from the projections of markers forming said alignment, the image sequence comprising a single cross-ratio per quadruplet of projections of markers, in which quadruplet the projections of markers are ordered in the predefined order depending on the rank number of respective projections of markers along the corresponding image straight line in the predefined first direction, and, when a set of projections of markers comprises at least five marker projections, the order of the cross-ratios in the image sequences is defined by the predefined rule along the corresponding image straight line; and for each marker projection forming said detected alignment, identifying the marker that generated it by attributing a cross-ratio sequence formed from the marker projections of said alignment to a portion of a cross-ratio sequence formed by markers of the test pattern comprising the same number of cross-ratios as the image sequence; and determining the geometric characteristics that the imaging device had during the acquisition of the projection of the test pattern from the positions of those projections of markers which were detected and the positions of the respective corresponding markers.

The method advantageously has at least one of the following features:

the step of detecting alignments is carried out by applying a Hough transform to the positions of the projections of markers that were detected in the step of detecting the projections of the markers;

the binary codes are sections of a series obtained by means of an LFSR of n bits.

BRIEF DESCRIPTION OF THE DRAWINGS

Other features and advantages of the invention will become apparent on reading the following detailed description, which is given by way of nonlimiting example and with reference to the appended drawings, in which.

From one figure to the next, the same elements have been referenced by the same references.

DETAILED DESCRIPTION

Figure 1:
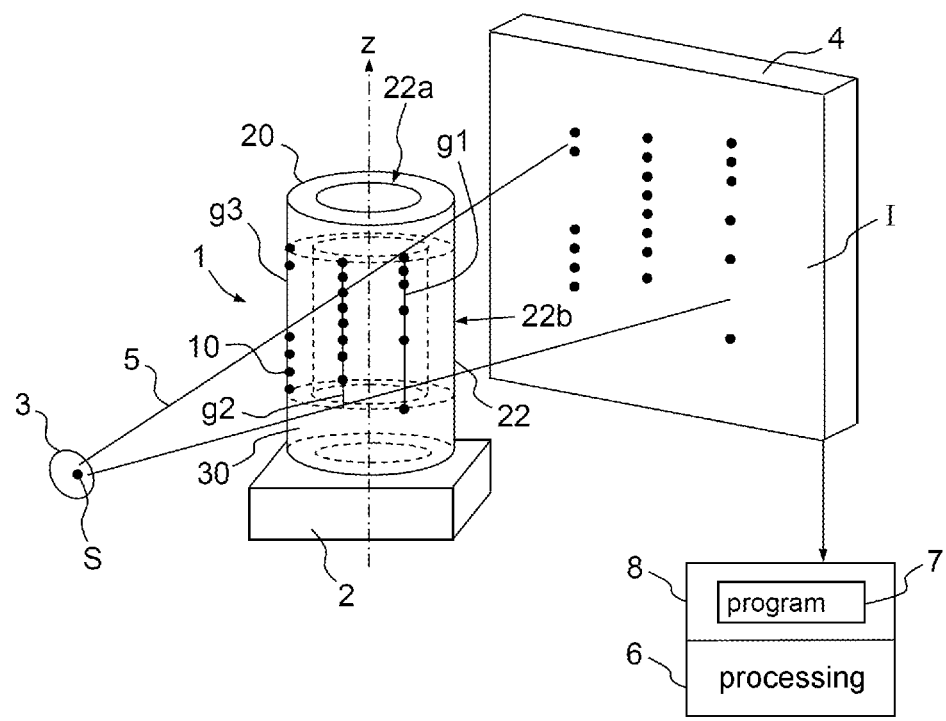
FIG. 1 schematically shows an x-ray imaging device in the configuration in which an image of the calibrating test pattern according to the invention is acquired.

FIG. 1 shows an x-ray imaging device. This imaging device comprises an x-ray source 3 comprising a focal point S and a planar detector 4. The imaging device advantageously comprises a device (not shown) allowing the source 3 and the planar detector 4 to be moved with respect to a holder 2 intended to receive an object to be imaged.

The calibrating test pattern 1 according to the invention is thus interposed between an x-ray source 3 and the planar detector 4. It is stationary with respect to the holder 2. The calibrating device also comprises a processing device 6 that is configured to implement at least one processing method contained in a program 7 stored in a program memory 8. The test pattern 1 comprises markers 10. Advantageously, a program containing a processing method allowing geometric characteristics of the imaging device to be calculated from the association between projections of the markers of the test pattern in respective 2D projections of the test pattern and the positions, in the test pattern, of the markers that generated these projections is stored in the memory 8. The projection I of the test pattern on the planar detector is schematically shown in FIG. 1.

The x-ray beam 5 emitted by the source 3 from the focal point S has a cone shape that widens en route from the source 3 to the planar detector 4. The geometrical operation employed in the production of an image is therefore a conical projection (or central projection) of the test pattern 1 deployed in the 3D space on the plane formed by the planar detector.

The calibrating test pattern 1 comprises a volume support 20 and a set of markers 10 borne by the volume support 20 and distributed in a three-dimensional pattern. The markers 10 are stationary with respect to the volume support 20. They are for example fastened to the surface of the support (as in FIG. 1) or embedded in the volume support 20. A volume support is a support having a three-dimensional form. The volume support is for example a hollow cylinder (as in FIG. 1) or a solid cylinder. The cylinder is advantageously rotationally symmetric about a z-axis. It has a circular directrix curve and a straight generatrix line perpendicular to the plane containing the directrix circle (directrix curve).

The markers 10 have a radiological absorbance providing contrast with respect to the volume support 20. In this way it is possible to reliably determine the positions of the images (or projections) of the respective markers in the image.

Preferably, the volume support 20 is transparent to x-rays. It is for example made of plexiglass, of PVC or of polycarbonate.

The markers absorb x-rays. They are for example made of stainless steel or any other similar material that is more absorbent to x-rays than the volume support 20.

The shape and size of the markers must be known with precision so as to facilitate their detection and the positioning of the mass points of their respective images, i.e. of their respective projections, in the acquired 2D images.

The markers 10 advantageously have the same size, the same shape and advantageously the same x-ray absorbance properties. This makes it possible to facilitate the detection and positioning of the projections or mass points of the projections of the markers in the 2D images. Advantageously, the markers have a spherical shape. This shape facilitates the detection and positioning of the projections of the markers in the 2D images since the conical projection of a sphere is always an ellipse similar to a disc and therefore easily positionable. As a variant, the markers have another shape. They are advantageously rotationally symmetric about respective axes of rotational symmetry. They are advantageously positioned so that their respective axes of rotational symmetry are substantially parallel to the z-axis or advantageously substantially parallel to the observable generatrices that will be described below. It may be a question of cylinders or bars that are elongate along respective axes. Advantageously, the markers are homogenous so as to have throughout their volume the same x-ray absorbance properties, thereby facilitating their detection and positioning.

In one variant, the set of markers comprises markers at least one of the aforementioned characteristics of which is different.

The positions of the respective markers 10 on the volume support 20 are known with enough precision to allow the geometric calibration to be carried out with the desired precision. For example, the position of the markers with respect to the volume support 20 is known with a precision of about 20 microns.

The distribution of the markers in the test pattern according to the invention has a plurality of characteristics.

The markers are distributed in subsets of markers. The markers of each subset of markers are distributed in a straight line. In other words, the markers of a given subset are placed on a straight line and spaced apart along the straight line. The straight lines along which the markers of respective subsets extend are parallel.

A sequence of cross-ratios, also called anharmonic ratios, may be constructed from the markers of each subset of markers. Each cross-ratio is calculated from distances between the markers of a quadruplet of markers of a given subset of markers.

Each cross-ratio is calculated from a quadruplet of markers, in which quadruplet the markers are ordered in a predetermined order depending on the rank number of the respective markers along the straight line in a predefined first direction.

This order is common to all the cross-ratios, ie to all the quadruplets of markers. In other words, one single cross-ratio is constructed per quadruplet of successive markers.

When a subset of markers comprises at least five markers, the corresponding sequence of cross-ratios comprises a plurality of cross-ratios. The order of the cross-ratios in each sequence is defined by a predefined rule common to all the sequences of cross-ratios. This rule is defined as a function of the order, i.e. the rank numbers, of the markers forming the respective quadruplets of markers of a subset (from which quadruplets the respective cross-ratios are calculated) along the corresponding straight line in a second predetermined direction. The order or rank number of a marker of a subset is its rank in a series formed by the markers of the corresponding subset, in which series the markers of the subset are classed by their order of succession along the corresponding straight line in the second direction.

The second direction is advantageously the first direction.

Figure 2:
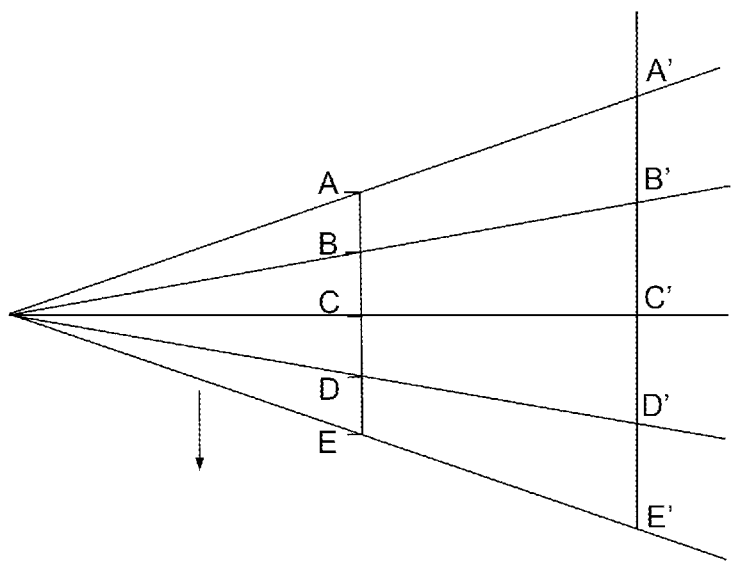
FIG. 2 schematically shows markers aligned in an observable straight line and projections of markers in another straight line.

For example, for four markers such as shown in FIG. 2, aligned along a straight line d, each cross-ratio is calculated in the direction of the arrow. If the cross-ratio function is denoted r, the cross-ratio r calculated for the markers A, B, C and D considered in this order along the corresponding straight line in the direction of the arrow is given by the following equation:

$$r(A, B, C, D) = \frac{\frac{\overline{CA}}{\overline{CB}}}{\frac{\overline{DA}}{\overline{DB}}}$$

The cross-ratio sequence constructed from the markers A, B, C, D and E is for example the following sequence:

r1=r(A,B,C,D)

followed by the cross-ratio r2=r(A,B, C, E)

followed by the cross-ratio r3=r(A,C,D,E)

followed by the cross-ratio r4=r(A,C, D,E)

followed by the cross-ratio r5=r(B,C,D, E).

Let us take a subset of N markers aligned along a straight line. N is an integer. These markers denoted $A_g$ have rank numbers g, where g=1 to N, along the straight line in the second direction.

Advantageously, the order of the cross-ratios in the sequence is defined in the following way:

```
if i is from 1 to N−3 then:
   (-if j is from i+1 to N−2 then:
      (-if k is from j+1 to N−1 then:
         (-if l is from k+1 to N then:
            (-insert the following cross-ratio in the sequence, the
            following cross-ratio being a cross-ratio calculated
            with the markers $A_{g=i}$, $A_{g=j}$, $A_{g=k}$, $A_{g=l}$,
            − l=l+1)
         − k=k+1)
      − j=j+1),
   −i=i+1).
```

Using this rule to construct the sequence makes it possible to guarantee the uniqueness of the cross-ratio sequences constructed from a set of markers, in particular when the markers are distributed as in the particular embodiment described in the description below, in which embodiment the values assigned to sites regularly spaced along a straight-line segment, considered in a given direction along the straight-line segment, form unique binary codes of n bits.

Each cross-ratio is calculated from one quadruplet of markers in which quadruplet the markers are ordered in a predetermined order of succession depending on the rank number of the respective markers along the corresponding straight line in a predefined first direction.

Advantageously, for the calculation of the cross-ratios, the order of the markers in each quadruplet of markers is the order of the markers along the straight line on which they are aligned in the predefined first direction. As a variant, the order of the markers in each quadruplet of markers is the order in the opposite direction to the predefined first direction.

Each sequence of cross-ratios is unique to the test pattern. In other words, the cross-ratio sequences formed from respective subsets of markers of the test pattern are all different. In other words, the cross-ratio sequences are different from one another. They are distinct.

It should be noted that it is possible to reliably determine a geometric acquisition configuration of the x-ray imaging device, by imaging the test pattern in this configuration, when it is possible to associate each projection of a marker in the 2D image with the marker of the test pattern that was used to generate the image. The test pattern according to the invention enables this association because each sequence of cross-ratios is unique. Specifically, because of the conical projection employed in the generation of a radiological image, a straight line remains a straight line and cross-ratios are unchanged. Therefore, as may be seen in FIG. 2, the projection of each subset of markers A, B, D, C, E is an alignment of a subset of projections of markers A', B', C', D', E'. The cross-ratio sequence formed from the projections of markers A', B', C', D', E' of the subset of projections of markers is identical to the cross-ratio sequence formed from the markers of the corresponding subset of markers A, B, C, D, E if the order of calculation of each of the cross-ratios from which the sequences are constructed is the same and if the same rule is used to define the order of the respective cross-ratios. Therefore, once the sequences have been constructed, it is possible to associate the projection of a marker with the corresponding marker by associating a sequence of a subset of markers with a sequence of projections of markers. It is not necessary to provide a reference marker.

The test pattern according to the invention allows a calibration to be achieved simply and reliably. Specifically, it is enough to detect the projections of the markers, to position them, to detect alignments of projections of markers, i.e. to form the respective subsets of projections of markers, to construct cross-ratio sequences from the projections of markers forming the respective alignments (or subsets) and to associate the respective cross-ratio sequences with respective cross-ratio sequences of the subsets of markers of the test pattern. Advantageously, the cross-ratio sequence formed from a subset of markers and attributed to that formed from a subset of projections of markers is that which, from all of the cross-ratio sequences formed from all the respective subsets of markers, has a minimum difference with the cross-ratio sequence formed from a subset of projections of markers. The operation for detecting alignments is an operation well known to and understood by those skilled in the art. This operation is simple and reliable. The same goes for the calculation of the inter-marker and inter-marker-projection distances.

Moreover, the solution according to the invention allows, because of the straight-line arrangement, erroneous positions to be corrected. Specifically, given that all the markers are each attributed to a projection of a marker at the same time, if the position of the projection of a marker is erroneous, the attribution of this projection to the corresponding marker will be achieved with a higher probability.

The construction of the sequences of cross-ratios of the projections of markers is independent of the geometry of the markers. It depends only on the distances separating the projections of the various markers, this limiting the risk of identifying erroneous sequences, whatever the angle of the image capture.

Advantageously, the subsets of markers are distributed, parallel to the z-axis, in respective straight-line segments having identical respective lengths and identical respective coordinates along the z-axis.

Advantageously, the straight-line segments are observable generatrices of a cylinder. Advantageously, the cylinder has rotational symmetry about the z-axis. It is for example a question of the cylinder 22.

Figures 3A, 3B:
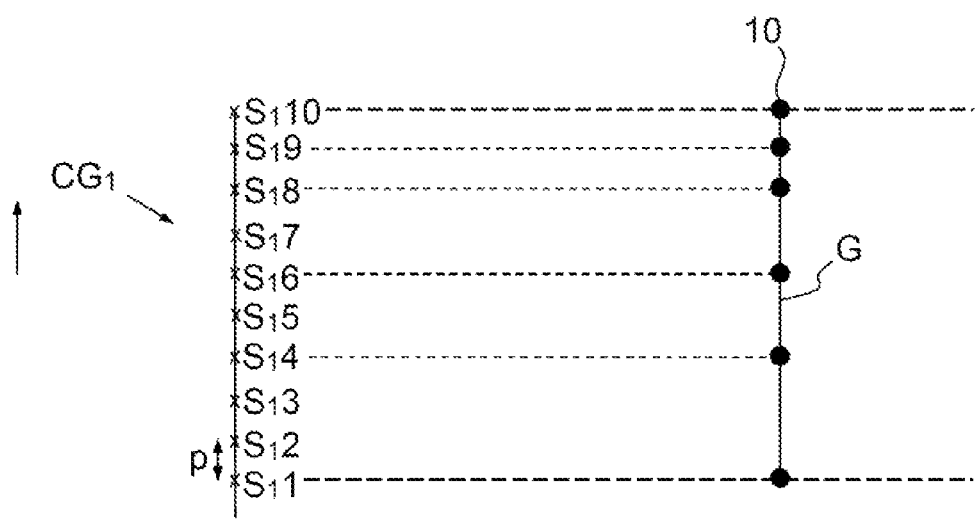
FIGS. 3a and 3b schematically show an observable generatrix of a test pattern according to the invention and the sites that it accommodates (FIG. 2a) and the markers placed on this generatrix (FIG. 2b)

This example is shown in FIGS. 1 and 3a and 3b.

In FIG. 1, the markers 10 are distributed along a plurality of observable generatrices g1, g2, g3 of a cylinder 22 and spaced apart along the directrix curve of the cylinder 30. In the nonlimiting embodiment in FIG. 1, the cylinder 22 is included in the cylinder formed by the volume body 20; it has the same z-axis and the surface formed by the straight generatrices of the cylinder 22 is a section of the outside surface 22b of the cylinder formed by the volume body 20. As a variant, the cylinder is any other cylinder integral with the volume body 20 and preferably coaxial with the volume body 20.

The observable generatrices g1, g2, g3 along which the markers 10 are distributed are spaced apart pairwise, along the directrix curve, by a fixed or variable distance. In other words, they are spaced apart pairwise by a fixed or variable angle about the z-axis of the directrix circle in the case of a cylinder of revolution. A plurality of markers are positioned on each observable generatrix g1, g2, g3 and spaced apart pairwise along said observable generatrix. In other words, the markers are arranged in straight lines.

FIGS. 3a and 3b show a preferred exemplary arrangement of the markers along the observable generatrix g1. In FIG. 3a, the sites $S_{i,j}$, where $j=1$ to 10, that the observable generatrix gi=1 comprises have been represented by crosses. In FIG. 3b, the markers positioned along this first observable generatrix have been shown. Each observable generatrix accommodates a first integer m of sites $S_{i,j}$, $j=1$ to m (where m=10 in the nonlimiting example of FIG. 1) capable of being occupied by a marker 10. These sites $S_ij$ are spaced apart by a fixed distance called the pitch p along said generatrix g1. In other words, any two consecutive sites considered along the observable generatrix, in a given direction shown by the arrow, are separated by a fixed distance p. It will be noted that in FIG. 3b the sites $S_1 1$, $S_1 4$, $S_1 6$, and $S_1 8$ to $S_1 10$ are occupied by a marker 10 and that the sites $S_1 2$, $S_1 3$, $S_1 5$ and S7 are free. Consecutive markers 10 along the straight generatrix g1 are therefore separated by a distance equal to a multiple of the pitch p.

Each site is assigned a first value (=1) or a second value (=0) respectively depending on whether it is occupied by a marker 10 or not, respectively. In the example in FIGS. 3a and 3b, the sites $S_1 1$, $S_1 4$, $S_1 6$, and $S_1 8$ to $S_1 10$ are assigned the value of 1 because they are occupied by a marker and the sites S2, $S_1 3$, $S_1 5$ and S7 are assigned a value of 0 because they are not occupied by a marker 10.

The values attributed to a second integer n of any consecutive sites considered along an observable generatrix g1, in a given direction (shown by the arrow) of the observable generatrix, form a binary informational unit (or word) composed of n bits. The expression "an informational unit of n bits" is understood to be synonymous with the expressions "a word", "a binary code" or "a binary sequence of n bits". In the embodiment in FIGS. 3a and 3b, the values attributed to the 10 sites comprised in the generatrix g1 form a code sequence comprising 3 code words of 8 bits each, i.e. three informational units each composed of 8 bits. These informational units 11, 12, 13 are formed from the values attributed to the sites S1 to S8, S2 to S9 and S3 to S10, respectively. These binary codes are the following:

I1: 10010101
I2: 00101011
I3: 01010111

The code sequence formed by the values attributed to the 10 sites of the generatrix g1 is the following: 1001010111.

Each informational unit of n bits considered for one observable generatrix in the given direction along said straight line, said direction being common to all the observable generatrices, must appear only once on the test pattern. In other words, each informational unit of n bits considered in the given direction is unique. It appears only once in all the observable generatrices. The predefined read-ont direction is the read-ont direction defined parallel to the axis of the cylinder. Advantageously, this direction is the first direction and/or the second direction.

By placing the markers in this way on the test pattern subsets of markers allowing unique respective cross-ratio sequences (such as defined above) to be formed on the test pattern are obtained simply and rapidly. Moreover, such a test pattern is easy to manufacture as it is easy to position the respective markers. Advantageously, each cross-ratio sequence comprising more than one cross-ratio is formed of sections of the sequence of unique cross-ratios in the test pattern. The sections of a sequence are read out in the same direction as the corresponding sequence. The sections of the sequence have a length W smaller than that of the sequence. The length W of the sections of sequence correspond to the number of cross-ratios in the sections of sequence. For example, in the example in FIGS. 3a and 3b, the sequence B1, B2, B3, B4 is formed from two unique sequences of length three: B1, B2, B3 and B2, B3, B4 or three unique sequences of length two: B1, B2 and B2, B3 and B3, B4.

This makes it possible to increase the robustness of the geometric calibration carried out using the test pattern according to the invention on truncation of the projection of the test pattern. Specifically, even if all the markers are not present in the projection, it is still possible to match, with a good degree of certainty, the marker projections present with the corresponding markers by associating sequences of projections of markers of length W with corresponding sections of marker sequences.

In the embodiment in FIGS. 3a and 3b, this has the following consequences. Each chain of markers placed along a generatrix of the cylinder having a length L (expressed in metres) represents a code sequence of m-bit length.

Advantageously, m is higher than n. In other words, the length L of the generatrices is larger than or equal to n×p. The probability of imaging a chain of markers of length n×p is higher than that of imaging a length m×p. However, the informational unit of n bits is unique in the test pattern, known and its position is known in the test pattern, thereby making it possible to reliably match the projections of markers present in this chain with the markers of this chain. As a variant m is equal to n.

In the embodiment in FIG. 3b, the observable generatrix g1 accommodates m=10 sites and the informational units are coded in n=8 bits. In preferred embodiments of the invention, these numbers m and n are much higher.

Typically, provision is made for informational units of n=16 bits and chains of markers representing code sequences of a length m comprised between 24 and 40 bits.

Advantageously, the chains of markers represent sequences of binary code comprising a proportion of 1 comprised between 7 and 18. Advantageously, the test pattern comprises at least 6 subsets of markers.

Advantageously, each cross-ratio sequence or section of cross-ratio sequence is unique in both directions. This makes it possible to decrease the risk of erroneous matches. However, this condition is not essential because this risk is limited because the informational units are produced along straight lines with invariant and predictable geometry in projection during an x-ray image capture.

Each informational unit is advantageously unique in the predefined direction and in another direction opposite to said direction.

Advantageously, the distribution of the observable generatrices g1, g2, g3 along the directrix curve 30, or more generally the straight lines along which the alignments are formed, is chosen so that, for all the projection conditions under which images are acquired during the calibration, i.e. for all the image-acquisition geometries used during the calibration (which geometries are defined by the positions of the source, of the detector and of the test pattern and their respective orientations), in which geometries the central radius of the beam emitted by the source 3 is inclined with respect to the z-axis by at most 45° and the detector is substantially perpendicular to the central radius, no marker projection overlaps another marker projection and/or so that if the marker projections issued from two subsets of markers do overlap, the projections of the markers of the other subsets of markers do not overlap. By central radius, what is meant is the radius located at the centre of the beam emitted by the x-ray source 3, i.e. the axis of symmetry of the beam emitted by the source 3. This makes it possible to make it easier to discriminate the projections of markers.

The manufacture of the calibrating test pattern according to the invention comprises a step of placing markers along the set of straight lines or set of observable generatrices with a distribution such that the respective cross-ratio sequences are unique. This distribution may be obtained by successive iterations of a step of placing markers, a step of constructing corresponding cross-ratio sequences and of verifying the uniqueness of the sequences.

Indeed, the markers are advantageously arranged so that the values attributed to any n consecutive sites considered along any one of the observable generatrices, in the direction of the observable generatrix, form an informational unit composed of n bits, the informational unit being unique in the test pattern in said direction. The markers may be distributed in a plurality of ways. They are for example distributed by successive iterations of a step of placing the markers, a step of constructing informational units and of verifying the uniqueness of the informational units or indeed by means of a linear feedback shift register of size n, each informational unit of n bits being a section, i.e. a sequence of n bits, of a series of length smaller than $2^n$ generated by an n-bit linear feedback shift register (LFSR). Use of an LFSR is well suited to actual implementation and is simple to implement. Moreover, the use of sequences of n bits of a series generated by an n-bit LFSR makes it possible to guarantee that unique sequences, i.e. unique informational units, will be obtained in the test pattern. Specifically a 16-bit LFSR guarantees that a series comprising 65535 completely different trains of 16 bits will be generated, the 16-bit trains being the consecutive states of the 16-bit LFSR.

Let us consider the case where each observable generatrix accommodates a number m higher than n of sites. For example, when n=16, then m is comprised between 24 and 40. The distribution of the markers between the sites of the generatrix for example forms a code corresponding to a series of m bits, which series is obtained by means of a 16-bit LFSR. This distribution is a simple distribution because there is no need for a step of verifying the uniqueness of the m-n 16-bit code sequences formed by the values attributed to these sites depending on whether they are occupied by a marker or not, as this uniqueness is guaranteed by the mathematical properties of the LFSR. Moreover, it guarantees that the code is unique in both directions.

Advantageously, to improve the reliability of the geometric calibration carried out by means of a test pattern according to the invention, the markers are distributed over the test pattern so that, for a known number of generatrices and of sites per generatrix, and for known degrees of occupation of the sites of respective generatrices, a difference between the binary codes formed by the values taken by the m consecutive sites accommodated by respective observable generatrices in the predefined direction is maximal. In other words, the chosen sequences in the series generated from the series obtained by the 16-bit LFSR are those that are most different. The calculated difference between two binary codes is for example the difference between the number of bits of value 1 of the result of the exclusive or of the two binary codes.

Figure 4:
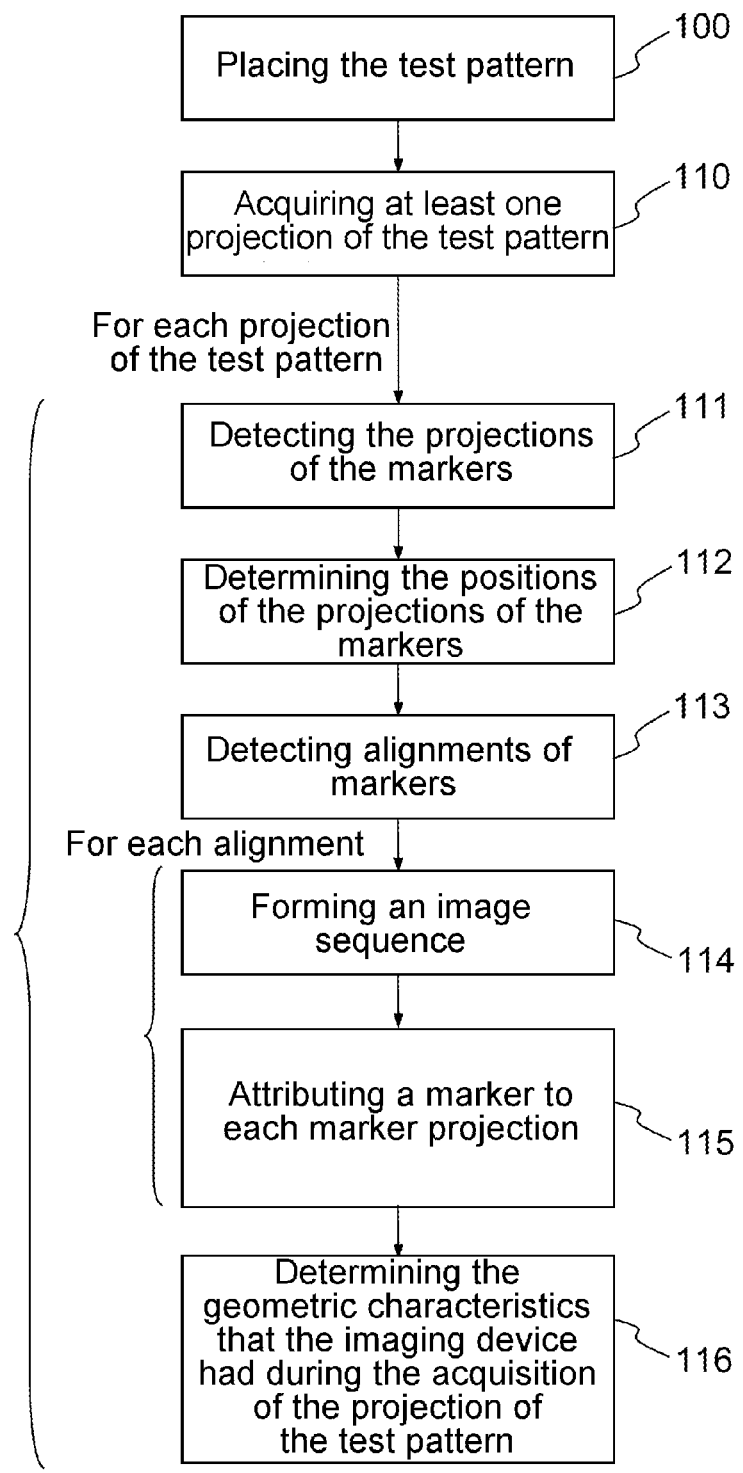
FIG. 4 shows a flowchart of the steps of the method according to the invention.

Another subject of the invention is a method for determining the geometric characteristics that the x-ray imaging device had during the acquisition of at least one image. The method uses a calibrating test pattern according to the invention. The method according to the invention comprises the following steps, which are shown in FIG. 4:

placing 100 the calibrating test pattern in a projection zone between the x-ray source and the x-ray detector;
acquiring 110 at least one projection of the test pattern in at least one imaging-device geometry; it is possible to acquire a plurality of projections in different geometries, for example with the source and/or of the detector in a plurality of angular positions on a circular path about the z-axis of the cylinder;

and, for at least one acquired projection:
detecting 111 the projections of markers in the projection; this step is implemented using a conventional method, such as for example, nonlimiting, a blob-detection method (blob standing for binary large object), or a shape-recognition and especially an ellipse-detection method;
determining 112 the positions of the projections of markers; this step may be carried out in step 111;
detecting 113, in the projection, alignments of projections of the markers in respective straight lines di that are what are called image straight lines; this step is for example carried out by a conventional method, for example of the linear-regression type or by means of a Hough transform; this step allows the straight lines on which the projections of the markers are aligned to be identified and the marker projections aligned on these respective straight lines to be identified; and
for each detected alignment i:
forming 114 a sequence, which is what is called the image sequence, of cross-ratios from the projections of markers forming said alignment, the image sequence comprising a single cross-ratio per quadruplet of projections of markers in which the projections of markers are ordered in the predefined order depending on the rank number of respective projections of markers along the corresponding image straight line in the predefined first direction and, when a set of projections of markers comprises at least five marker projections, the order of the cross-ratios in the image sequences is defined by the predefined rule along the corresponding image straight line (this rule is therefore common to all the alignments, it is defined as a function of the order or rank number of the respective marker projections forming the quadruplets of marker projections used to generate the respective cross-ratios along the corresponding image straight line in the second predetermined direction; this rule is the same as the rule used in construction of the sequences of cross-ratios); and
for each marker projection forming said detected alignment, identifying 115 the marker that generated it by attributing a cross-ratio sequence formed from the marker projections of said alignment to a portion of a cross-ratio sequence formed by markers of the test pattern comprising the same number of cross-ratios as the image sequence; and
determining 116 the geometric characteristics that the imaging device had during the acquisition of the projection of the test pattern from the positions of those projections of markers which were detected and the positions of the respective corresponding markers. This step especially consists in calculating a matrix allowing the 2D space to be projected onto the 3D space. It is for example carried out using the Faugeras-Toscani algorithm or the Levenberg-Marquardt algorithm.

During step 115, the marker that has generated marker projection is identified by associating a cross-ratio sequence formed from the marker projections of said alignment to a portion of a cross-ratio sequence formed by markers of the test pattern comprising the same number of cross-ratios as the image sequence.

The step 115 of identifying the markers that generated each of the detected marker projections advantageously consists in identifying which test-pattern marker-sequence portion has a minimum difference with the image sequence or is identical to the image sequence. The minimized difference is, for example, the variance of the difference of the two sequences of cross ratios or the variance of a weighted difference of the two sequences of cross ratios, in order to compensate for the fact that the cross ratios are all different whereas any error is, for its part, substantially identical.

Advantageously, the step of detecting alignments is carried out by applying a Hough transform only to the positions of the projections of markers detected in the step of detecting the projections of the markers. This amounts to applying a Hough transform to a binary image comprising a uniform background and pixels having a contrast with respect to the uniform background and the respective positions of which are the positions of the marker projections that were detected in step 112. This makes it possible to detect the straight lines on which the pixels are aligned and to prevent the Hough transform from detecting the outlines of the projections of the markers. The risk of error is therefore limited. Moreover this simplifies the Hough algorithm and limits calculation time.

The invention claimed is:

1. A calibrating test pattern comprising:
a volume support equipped with markers with a radiological absorbance providing contrast with respect to the volume support, the markers being distributed in a three-dimensional pattern and in subsets distributed in substantially parallel straight lines, such that sequences of cross-ratios are constructed from the subsets of markers, each sequence of cross-ratios comprising a single cross-ratio for each quadruplet of markers,
wherein quadruplets of the markers are in an order depending on the rank number of the respective markers along the straight line on which they are aligned in a first direction, said order being common to all of the cross-ratios, and when a subset of markers comprises at least five markers, the order of the cross-ratios in the respective sequences of cross-ratios is defined by a predefined rule common to all of the sequences of cross-ratios, each of the sequences of cross-ratios being different.

2. The calibrating test pattern according to claim 1, wherein all of the markers have substantially the same size and substantially the same shape.

3. The calibrating test pattern according to claim 1, wherein the straight lines are observable generatrices of a cylinder.

4. The calibrating test pattern according to claim 1, wherein for all of the projection conditions under which images are acquired during calibration, no marker projection overlaps another marker projection and/or when the marker projections issued from two subsets of markers do overlap, the projections of the markers of the other subsets of markers do not overlap.

5. The calibrating test pattern according to claim 1, wherein the subsets of markers are distributed in respective observable straight-line segments parallel to a z-axis, the straight-line segments being of the same length and having the same coordinates along said z-axis, each straight-line segment accommodating a first positive integer m of sites capable of being occupied by a marker, any two consecutive sites considered along said observable segment being spaced apart by a pitch, each site respectively being assigned a first value or a second value depending on whether the site is occupied by a marker or not, the markers being distributed so that the values attributed to a second positive integer n, at most equal to m, of any consecutive sites considered in a given direction along respective straight-line segments form respective binary codes composed of n bits, each binary code composed of n bits formed in said direction being unique.

6. The calibrating test pattern according to claim 5, wherein the first positive integer m is higher than the second positive integer n.

7. The calibrating test pattern according to claim 5, wherein the markers are distributed over the test pattern, such that, for a known number of straight-line segments and of sites per straight-line segments, and for known degrees of occupation of the sites of straight-line segments, a difference between the binary codes formed by the values taken by the m consecutive sites accommodated by respective straight-line segments in the direction is maximal, the binary codes being sections of a series obtained by means of a LFSR of n bits, m being lower than or equal to n.

8. The calibrating test pattern according to claim 1, wherein the order of the cross-ratios in each cross-ratio sequence constructed from a subset of markers aligned on a straight line is defined in the following way:

--- for markers denoted $A_g$ having rank numbers g = 1 to N along the straight line in a second direction,
  if i is from 1 to N−3 then:
    (-if j is from i+1 to N−2 then:
      (-if k is from j+1 to N−1 then:
        (-if l is from k+1 to N then:
          (-insert the following cross-ratio in the sequence, the following cross-ratio being a cross-ratio calculated with the markers $A_{g-i}$, $A_{g-j}$, $A_{g-k}$, $A_{g-l}$,
          − l=l+1)
        − k=k+1)
    − j=j+1),
  −i=i+1),

--- where N is a positive integer.

9. The calibrating test pattern according to claim 1, wherein the order of the markers in each quadruplet of markers is the order of the markers along the straight line on which they are aligned in the first direction.

10. A method for determining geometric characteristics of an x-ray imaging device for producing three-dimensional projections of an object by reconstruction based on two-dimensional projections of said object, said method using a calibrating test pattern according to claim 1, the method comprising the following steps:
placing the calibrating test pattern in a projection zone between an x-ray source and an x-ray detector;
acquiring at least one projection of the calibrating test pattern in at least one imaging-device geometry defined by the positions of the source, the test pattern, the detector, and relative orientations;
and, for each projection of the test pattern:
detecting the projections of markers in the projection;
determining the positions of the projections of markers in the projection;
detecting alignments of projections of the markers in respective image straight lines; and
for each alignment of projections of markers:
forming an image sequence of cross-ratios from the projections of markers forming said alignment, the image sequence comprising a single cross-ratio per quadruplet of projections of markers in which the projections of markers are ordered in the order depending on the rank number of respective projections of markers along the corresponding image straight line in the predefined first direction, and, when a set of projections of markers comprises at least five marker projections, the order of the cross-ratios in the image sequences is defined by the predefined rule along the corresponding image straight line; and for each marker projection forming said detected alignment, identifying the generating marker by attributing a cross-ratio sequence formed from the marker projections of said alignment to a portion of a cross-ratio sequence formed by markers of the test pattern of the same number of cross-ratios as the image sequence; and determining the geometric characteristics that the imaging device had during the acquisition of the projection of the test pattern from the positions of those projections of markers which were detected and the positions of the respective corresponding markers.

11. The calibrating method according to the claim 10, wherein the step of detecting alignments is carried out by applying a Hough transform to the positions of the projections of markers that were detected in the step of detecting the projections of the markers.

12. A process for manufacturing a calibrating test pattern according to claim 5, comprising a step of distributing the markers such that the binary codes are sections of a series obtained by means of an LFSR of n bits.

* * * * *